United States Patent [19]

Weinstock et al.

[11] Patent Number: 4,477,455

[45] Date of Patent: Oct. 16, 1984

[54] KALIURETIC COMPOSITIONS CONTAINING TMPPT

[75] Inventors: Joseph Weinstock, Phoenixville; Virgil D. Wiebelhaus, Springfield, both of Pa.

[73] Assignee: SmithKline Beckman Corporation, Philadelphia, Pa.

[21] Appl. No.: 464,076

[22] Filed: Feb. 4, 1983

[51] Int. Cl.$^3$ .............................................. A61K 31/505
[52] U.S. Cl. ....................................... 424/251; 544/251
[58] Field of Search ......................... 424/251; 544/251

[56] References Cited

U.S. PATENT DOCUMENTS 2,561,324  7/1951  De Garmo ...................... 544/251 X
2,581,889  1/1952  Timmis ........................... 544/251 X

OTHER PUBLICATIONS

Kakemi, K., et al., *Chem. Pharm. Bull.,* 16, (10), 2018–2022, (1968).
Derwent, Abstract of Japan, 51, 001496, 1/8/1976.

*Primary Examiner*—Richard A. Schwartz
*Attorney, Agent, or Firm*—William H. Edgerton; Richard D. Foggio; Alan D. Lourie

[57] ABSTRACT

1,3,7,9-Tetramethylpyrimido[5,4-g]pteridine-2,4,6,8-(1H,3H,7H,9H)-tetraone is an active ingredient in pharmaceutical compositions useful for inducing kaliuresis. It, also, can be used in combination with a distal tubule acting diuretic to give an improved diuretic effect.

8 Claims, No Drawings

KALIURETIC COMPOSITIONS CONTAINING TMPPT

This invention relates to new pharmaceutical compositions and methods which utilize 1,3,7,9-tetramethylpyrimido[5,4-g]pteridine-2,4,6,8-(1H,3H,7H,9H)-tetraone as an active ingredient to induce kaliuresis in patients in need thereof.

BACKGROUND OF THE INVENTION 1,3,7,9-Tetramethylpyrimido[5,4-g]pteridine-2,4,6,8-(1H,3H,7H,9H)-tetraone (the tetraone) is a compound which has been described in the prior art to be a chemical which has non-specific utility. U.S. Pat. No. 2,561,324, for example, alleged it to be a new chemical compound which had utility either as a "pharmaceutical" or as an intermediate in the preparation of other organic chemicals which might have utility as therapeutic agents.

U.S. Pat. No. 2,581,889 disclosed a method for preparing pyrimidopyrazines in general. The preparation of the tetraone, which is the active ingredient of the present invention, was described in Examples 9 and 10. Again, no specific biological activity was described for this compound.

Japanese Pat. No. 51001496 alleged that the N-oxide of the tetraone had anti-cancer activity in mice.

None of the art, therefore, has described any specific pharmaceutical utility for 1,3,7,9-tetramethylpyrimido[5,4-g]pteridine-2,4,6,8-(1H,3H,7H,9H)-tetraone. Certainly, no utility which would suggest any effect on the renal system is described by the art known to the applicants.

DESCRIPTION OF THE INVENTION

This invention comprises pharmaceutical compositions and methods for inducing kaliuresis in patients in need of such treatment which employ a kaliuretic, nontoxic quantity of 1,3,7,9-tetramethylpyrimido[5,4-g]pteridine-2,4,6,8-(1H,3H,7H,9H)-tetraone (I) which has the structural formula:

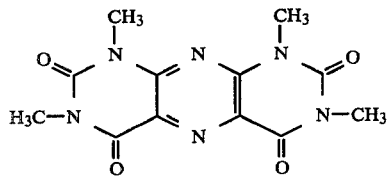

An effective, nontoxic quantity of the active ingredient for incorporation into each dosage unit is selected from the range of about 25-350 mg, especially 75-250 mg, of the dione. The dosage units are usually adapted for the preferred oral administration.

The dosage unit compositions of this invention are prepared by standard pharmaceutical techniques by incorporation of the active ingredient into a pharmaceutical carrier, for example, in the form of a tablet, capsule, troche or powder for suspension or solution. A nontoxic, kaliuretic quantity of the dione compound of formula I is screened, sized and mixed together with a filler if need be, for example, talc, lactose, terra alba, magnesium stearate, agar, pectin, acacia, gelatin or stearic acid. The mixed active ingredient and filler are, then, filled into a hard gelatin capsule.

Alternatively, the ingredients are tabletted using lubricants and granulating agents. Also, liquid carriers for the tetraone can be used, for example, peanut oil, sesame oil, olive oil or water. Such liquid-solid mixtures are filled into soft gelatin capsules or, in case of a sterile, isotonic suspension for parenteral use, into a unit or multidose vial for injection. In the preparation of the dosage units of this invention, the pharmaceutical chemist should note that the dione chemicals has low water solubility.

If the kaliuretic agent is desired to be in a time or controlled release formulation, coating agents are used in preparing the dosage units such as glyceryl distearate, wax, polyvinylpyrrolidone, zein, ethylcellulose caster wax, polymethacrylates, cellulose acetate butyrate, a cross-linked polymeric film, for example, one formed from prepolymers of an unsaturated dicarboxylic acid and an ethylene compound, or acid copolymers formed from acrylic or methacrylic acid monomers.

The methods of using the active tetraone of formula I comprise administering internally, preferably orally but also parenterally, to a human or animal patient in need of kaliuresis, a kaliuretically effective, nontoxic quantity of the tetraone. Such quantities are selected from the dose ranges given above for an average patient of 70 kg body weight. An effective program of treatment is administration of such a dosage unit from 1-5 times, usually 3 to 4 times, daily by oral administration. Extended release or parenteral administration, the latter such as by intravenous use, usually involves unit quantities smaller than those which are given above as illustrative of this invention.

The abnormal conditions of the subject to be treated will be any that require excretion of potassium ion with proportionally little increase in saluretic activity. Such patients include those having hyperkalemia from potassium overdose, acidosis, Addison's disease, terminal renal failure, improper use of potassium sparing diuretics, the conditions of hypo-reninism and hypo-aldosterism or renal insufficiency due to any cause.

In addition to the aspects of this invention described above, an unexpected synergistic effect of the dione was discovered when it is combined with an effective, nontoxic quantity of a diuretic of the potassium sparing category.

Such diuretics are known to act at the distal convoluted portion of the renal tubules and are known to the art as distal nephron diuretics [T. O. Morgan, Drugs 15 152 (1978)]. They are used as both diuretics and antihypertensives. Examples of such diuretics are triamterene (50 mg), amiloride, (5 mg), spironolactone (25, 50 or 100 mg) or 1,4-dimorpholino-7-phenylpyrido[3,4-d]pyridazine (10 mg). The clinical dosage unit quantities of such compounds used in the art are given above in parentheses after each exemplary compound. The dosage unit of the diuretic compound is, therefore, chosen from the range of 5-100 mg. These are administered from 1-5 times daily.

The doses of the prior art diuretics and the dione ingredient to be used in combination are, most usefully, chosen from the lower part of the respective dosage unit ranges of the two components. The combination with the tetraone increases the kaliuretic effect of the potassium sparing diuretic somewhat but, more unexpectedly, increases its natriuretic effect from 100-400%. The combinations of this aspect of the present invention are prepared in dosage units using quantities of each component as described above. The combinations are administered internally to a patient in need of conventional diuretic therapy. Oral administration is preferred, from 1-5 times daily.

This invention is based on a biological profile of the active tetraone which is derived from standard pharmacological protocols, such as those described by V. Wiebelhaus et al., Journal of Pharmacology and Experimental Therapeutics 149, 397 (1965) in which results of the tests using the marketed distal tubule diuretic product, triamterene, are disclosed.

The sodium deficient rat protocol is designed to emphasize the effect of a compound on potassium ion excretion while minimizing the effect on sodium ion excretion. Each of the figures in Table I represents an average of eight animals.

TABLE I

| Compound | mg/kg/p.o. | Sodium Deficient Rat mg/Rat Na+ | mg/Rat K+ | Na/K |
|---|---|---|---|---|
| Tetraone | 0 | 1.33 | 5.57 | 0.41 |
| | 15 | 0.96 | 23.44 | 0.07 |
| | 30 | 1.13 | 49.59 | 0.04 |
| Tetraone | 0 | 0.43 | 8.70 | 0.09 |
| | 15 | 0.70 | 56.38 | 0.02 |
| | 30 | 1.76 | 71.00 | 0.04 |
| Triamterene | 0 | 0.39 | 5.90 | 0.11 |
| Tetraone | 30 | 8.77 | 7.14 | 2.05 |
| Tetraone | 15 | 0.43 | 54.40 | 0.01 |
| | 30 | 0.65 | 67.10 | 0.02 |
| Triamterene plus | 15 | 18.59 | 22.94 | 1.38 |
| Tetraone | 30 | | | |
| Triamterene plus | 30 | 27.02 | 41.32 | 1.11 |
| Tetraone | 30 | | | |
| Amiloride HCl | 0 | 0.56 | 6.72 | 0.14 |
| Tetraone | 15 | 10.54 | 2.33 | 7.94 |
| | 30 | 0.46 | 72.08 | 0.01 |
| Amiloride HCl plus | 15 | 24.41 | 17.35 | 2.44 |
| Tetraone | 15 | | | |
| Amiloride HCl plus | 15 | 43.69 | 26.60 | 2.79 |
| Tetraone | 30 | | | |

In Table I, the tetraone active ingredient of this invention demonstrates a potent kaliuretic effect along with little effect on natriuresis when administered by itself. Combined with either triameterene or amiloride, the tetraone demonstrates a potent increase in natriuresis. Note, when compared with the sum of the two individual effects, a remarkable increase of sodium ion excretion was recorded by the combination with an unexpectedly small increase of potassium ion excretion.

Other standard diuretic tests were, also, carried out on the tetraone. In the saline-loaded rat protocol, doses of 30 and 60 mg/kg p.o. of the tetraone raised urine excretion 126 and 125% over controls, respectively. In anti-ADH rats, which are prepared by giving a water load and vasopressin, the tetraone significantly increased potassium ion excretion at 10 and 30 mg/kg p.o. In the adrenalectomized, water loaded rat test which is a measure of glucocorticoid activity, as expected, no increase of kaliuretic, natriuretic or diuretic effect was noted.

In the 24-hour dog test, the tetraone at 25 mg/kg p.o. gave three times the kaliuresis of hydrochlorothiazide and twice that of furosemide at maximal effective doses of these two known diuretics. No increase of triamterene- or amiloride-induced natriuresis was observed.

In a toxicity dose range test in dogs, no side effects were noticed after 5 or 15 mg/kg p.o. of the tetraone. Dry mouth was noticed at 25 mg/kg. In the rat dose range, no side effects were noticed up to 300 mg/kg orally of the tetraone at which dose slightly decreased motor activity was observed. In other tests for biological activity of the tetraone, slight anti-secretory, hypotensive and anti-inflammatory activities were observed.

The following examples are designed to illustrate this invention but not to limit its practice.

EXAMPLE 1

| Ingredients | Amount, mg: |
|---|---|
| 1,3,7,9-Tetramethylpyrimido[5,4-g]-pteridine-2,4,6,8-(1H,3H,7H,9H)—tetraone | 125 |
| Triamterene | 50 |
| Sucrose | 25 |
| Calcium Sulfate, dihydrate | 50 |
| Talc | 5 |
| Stearic Acid | 3 |
| Starch | 10 |

The active ingredients, sucrose and calcium sulfate are mixed, granulated using, a hot 10% gelatin solution, meshed and dried. After mixing with the remaining ingredients, the mixture is compressed into a scored tablet.

The tablet, whole or broken, is administered orally three times daily to a patient in need of diuretic therapy.

EXAMPLE 2

| Ingredients | Amount, mg: |
|---|---|
| 1,3,7,9-Tetramethylpyrimido[5,4-g]-pteridine-3,4,6,8-(1H,3H,7H,9H)—tetraone | 100 |
| Lactose | 175 |
| Magnesium Stearate | 2 |

The ingredients are mixed and filled into a hard gelatin capsule. Such compositions are administered to a patient in need of kaliuretic treatment from 2-4 times daily.

EXAMPLE 3

| Ingredients | Amount, mg: |
|---|---|
| 1,3,7,9-Tetramethylpyrimido[5,4-g]-pteridine-3,4,6,8-(1H,3H,7H,9H)—tetraone | 50 |
| Amiloride | 5 |
| Lactose | 150 |
| Magnesium Stearate | 5 |

The ingredients are mixed and filled into a hard gelatin capsule. Such are administered orally to a hypertensive patient from 3-5 times daily.

What is claimed is:

1. A pharmaceutical composition consisting of a tablet or capsule dosage unit for oral administration and having kaliuretic activity which comprises a nontoxic, kaliuretic quantity of 1,3,7,9-tetramethylpyrimido[5,4-g]pteridine-2,4,6,8-(1H,3H,7H,9H)-tetraone combined with a pharmaceutical carrier, said quantity being selected from the range of 25-350 mg.

2. The method of producing kaliuresis in a patient in need thereof comprising administering orally or parenterally to said patient a nontoxic, kaliuretic quantity of 1,3,7,9-tetramethylpyrimido[5,4-g]pteridine-2,4,6,8-(1H,3H,7H,9H)-tetraone.

3. The method of claim 2 in which the administration is oral and the quantity is selected from the unit dosage range of 50–350 mg administered from 1–5 times daily.

4. The method of claim 2 in which the administration is oral and the quantity is 100 mg administered from 3–4 times daily.

5. A pharmaceutical composition having diuretic activity in an oral dosage unit form comprising:

(A) a nontoxic, kaliuretic quantity of 1,3,7,9-tetramethylpyrimido[5,4-g]pteridine-2,4,6,8-(1H,3H,7H,9H)-tetraone; and (B) a nontoxic, diuretic quantity of a distal nephron diuretic.

6. The composition of claim 5 in which the diuretic is triamterene.

7. The composition of claim 5 in which the diuretic is amiloride.

8. The composition of claim 5 in which the quantity of the tetraone is selected from 25–350 mg.

* * * * *